(12) United States Patent
Koganov et al.

(10) Patent No.: US 11,779,624 B2
(45) Date of Patent: Oct. 10, 2023

(54) BIOACTIVE COMPOSITIONS FROM FRUIT AND METHODS FOR THEIR PRODUCTION

(71) Applicant: ISP INVESTMENTS LLC, Wilmington, DE (US)

(72) Inventors: Michael Koganov, White Plains, NY (US); Olga Dueva-Koganov, White Plains, NY (US); Artyom Duev, White Plains, NY (US); Steven Micceri, Milford, CT (US)

(73) Assignee: ISP INVESTMENTS LLC, Wilmington, DE (US)

( * ) Notice: Subject to any disclaimer, the term of this patent is extended or adjusted under 35 U.S.C. 154(b) by 260 days.

(21) Appl. No.: 17/208,700

(22) Filed: Mar. 22, 2021

(65) Prior Publication Data
US 2021/0205393 A1 Jul. 8, 2021

Related U.S. Application Data

(62) Division of application No. 16/376,953, filed on Apr. 5, 2019, now Pat. No. 10,953,061, which is a division of application No. 14/769,877, filed on Aug. 24, 2015, now abandoned, application No. 17/208,700 is a division of application No. 14/769,877, filed as application No. PCT/EP2014/054758 on Mar. 12, 2014, now abandoned.

(60) Provisional application No. 61/792,709, filed on Mar. 15, 2013.

(51) Int. Cl.
| | |
|---|---|
| A61K 36/73 | (2006.01) |
| A61K 36/752 | (2006.01) |
| A61K 36/81 | (2006.01) |
| A61K 36/88 | (2006.01) |
| A61K 36/185 | (2006.01) |
| A61K 36/45 | (2006.01) |
| A61K 36/736 | (2006.01) |

(52) U.S. Cl.
CPC ............ *A61K 36/73* (2013.01); *A61K 36/185* (2013.01); *A61K 36/45* (2013.01); *A61K 36/736* (2013.01); *A61K 36/752* (2013.01); *A61K 36/81* (2013.01); *A61K 36/88* (2013.01); *A61K 2236/31* (2013.01); *A61K 2236/37* (2013.01)

(58) Field of Classification Search
None
See application file for complete search history.

(56) References Cited

U.S. PATENT DOCUMENTS

2011/0305804 A1* 12/2011 Olcese ............... A23L 2/82
426/324

OTHER PUBLICATIONS

Moake (Comprehensive Reviews in Food Science and Food Safety (2005), vol. 1, pp. 8-21).*

* cited by examiner

*Primary Examiner* — Susan Hoffman
(74) *Attorney, Agent, or Firm* — William J. Davis; Nathalie Tietcheu

(57) ABSTRACT

The present invention relates to composition comprising a bioactive fractions (ingredients) derived from fruit juice of an Apple (*Pyrus malus*) produced by processing the fresh fruit of apple under conditions effective to yield a bioactive fraction that is substantially free of protein and patulin. The present invention also relates to compositions having anti-oxidant and free radical scavenging properties and suitable for topical applications, oral applications and functional drink applications.

10 Claims, No Drawings

BIOACTIVE COMPOSITIONS FROM FRUIT AND METHODS FOR THEIR PRODUCTION

CROSS-REFERENCE

This application is a divisional of U.S. application Ser. No. 16/376,953 filed on Apr. 5, 2019, now U.S. Pat. No. 10,953,061, which was the divisional application Ser. No. 14/769,877 filed on Aug. 24, 2015, now abandoned, which was a national stage of PCT Application No. PCT/EP2014/054758 filed Mar. 12, 2014 which claims priority of the provisional application No. 61/792,709 filed Mar. 15, 2013, each of which are hereby incorporated by reference herein in their entirety.

FIELD OF THE INVENTION

The present invention relates to bioactive fractions (ingredients) that include isolated bioactive fractions derived from fruit juices that are either free of or substantially free of patulin and protein. Further, the bioactive fractions have antioxidant, free radical scavenging, moisturizing and buffering activities and properties.

BACKGROUND OF THE INVENTION

Apples are a part in all food diets and their therapeutic value is well known for different illnesses (determines the absorption of gastric secretions, the elimination of toxins, has diuretic effect). Firmness and sugar content are important quality attributes that directly influence consumers on purchasing fresh apple fruit. Organic acids are an important component of fruit flavor and, together with soluble sugars and aromas, contribute to the overall organoleptic quality of fresh apple fruits. Malic acid is the predominant organic acid in apple fruits [Campeanu, G., G. Neata and G. Darjanschi (2009). Chemical composition of the fruits of several apple cultivars growth as biological crop. Notulae Botanicae Horti Agrobotanici Cluj-Napoca 37(2):161-164].

Malic acid is the major component of apple that is founding to maintain the liver in a healthy condition and it help in digestion process. The content of organic acids might be also of interest in that certain acids may lead to a lowering of the postprandial blood glucose and insulin responses [Suni, M., M. Nyman, N.-A. Eriksson, L. Björk and I. Björck (2000). Carbohydrate composition and content of organic acids in fresh and stored apples. J. Sci. Food Agric. Journal of the Science of Food and Agriculture 80:1538-1544]. Apples, and especially apple peels, have been found to have a potent antioxidant activity and can greatly inhibit the growth of liver cancer and colon cancer cells. The total antioxidant activity of apples with the peel was approximately 83 μmol vitamin C equivalents, which means that the antioxidant activity of 100 g apples (about one serving of apple) is equivalent to about 1500 mg of vitamin C. However, the amount of vitamin C in 100 g of apples is only about 5.7 mg. Vitamin C in apples contributed less than 0.4% of total antioxidant activity [Boyer, J. and R. H. Liu (2004).

Apple phytochemicals and their health benefits are well known. Nutrition Journal 3(5): http://www.nutritionj.com/content/3/1/5]. (Boyer and Liu, 2004). Lee et al. [Lee, K, Y. Kim, D. Kim, H. Lee and C. Lee (2003). Major phenolics in apple and their contribution to the total antioxidant capacity. Journal of Agriculture and Food Chemistry 51:6516-6520] found that the average concentration of ascorbic acid among six apple cultivars was 12.8 mg/100 g fruit. Apples contain a large concentration of flavonoids, as well as a variety of other phytochemicals, and the concentration of these phytochemicals may depend on many factors, such as cultivar, harvest, storage and processing of the apples. Consumers are becoming more interested in the content of the health-promoting compounds in fruit because of their antioxidant activity [Robards, K., P. D. Prenzler, G. Tucker, P. Swatsitang and W. Glover (1999).]

Phenolic compounds and their role in oxidative processes in fruits is also well known. Food Chem. 66:401-436]. Fruit juice is a fluid expressed from various fruits by crushing and pressing. It can be clear, cloudy or pulpy. Term apple cider in the United States is often used to mean cloudy, unfermented, unpreserved apple juice; it contains intracellular and extracellular water, carbohydrates (sugars, pectin, hemicellulose, cellulose, starch), protein, lipids, organic acids (malic, citric, tartaric, acetic, ascorbic), tannins, phenolic acids and complex phenols, vitamins, minerals, fiber, carotenoids, anthocyanins, traces of chlorophyll. These solids are categorized as soluble, which is readily expressed in the juice and insoluble, consisting primarily of the press residue. Despite the small amounts of some compounds, they can influence dramatically the appeal, stability, or health value of the fruit. Many intrinsic (fruit-specific) and extrinsic (process-dependent) factors influence juice composition. If the juice is processed or clarified, it is then called apple juice [Principles and practices of small and medium-scale fruit juice processing by R. P. Bates, J. R. Morris and P. G. Crandall FAO (2001) Agricultural Services Bulletin].

Malic acid and/or sodium malate that are present in apple juice are being used in cosmetic products and food for pH adjustment and effective buffering purposes, as well as flavor additive. Malic acid is an alpha-hydroxy acid (AHA) which may have some exfoliating action, and there are products which claim it in that capacity. Sodium malate might have humectant and moisturizing properties. Malic acid is naturally and predominantly found in apples; it acts as gentle exfoliator while providing nutrients to the skin/scalp as component of tricarboxylic acid cycle (TCA cycle) or the Krebs cycle.

Thus, apple's composition, known health benefits of apple and its purported ability to keep the doctor away, suggests that this fruit is expected to have a long life in drink, skin, hair and oral care products and applications. However, there are certain undesirable components that are present in apple fruit and in apple juice, namely patulin and protein.

Patulin or 4-Hydroxy-4H-furo[3,2-c] pyran-2(6H)-one is a mycotoxin produced by certain species of the genera *Aspegillus* and *Penicillium*. Apples used for processing into juice production could be inadvertently damaged during transportation. The certain percentage of fruit with varying degrees of damage (rot) can contain patulin. It is common in apples and other fruit that is damaged prior to processing for juice production. Patulin is produced by various molds, which primarily infect the moldy part of apples. Removing the moldy and damaged parts of the fruit may not eliminate all the patulin because some of it may migrate into sound parts of the flesh. Also, patulin can be produced within the fruit, even though it may not be visibly moldy. If moldy apples are used to produce apple juice, the patulin goes into the juice. It is not destroyed by heat treatments such as the pasteurization process. Patulin is a natural human toxin and therefore can have genetic affects within cells, including a developing fetus, the immune system and the nervous system. The recommended advisory level is 50 microgram of patulin/kg in apple juice [Guidance on the control of patulin in directly pressed apple juice, http://www.newark-sherwooddc.gov.uk/ppimageupload].

*Penicillium expansum*, is one such fungus and it is responsible for decomposition of apples and other fruit. The United Kingdom Ministry of Agriculture, Fisheries and Food in its Food Surveillance Paper No. 36 (1993) "Mycotoxins "Third Report" indicates that *Penicillium expansum* which produces patulin is a common problem in a diverse range of product (e.g. apples, peaches, pears, bananas, pineapples, apricots, cherries and grapes). They indicate that for apple juices patulin levels are generally higher in cloudy juices than in clear juices (highest levels in their data showed as 434 microgram/kg and 118 microgram/kg respectively). Mycotoxins are undesirable in the ingredients from apple or other fruit because of their toxicity to animals and potential toxicity to human beings. The toxic activity of patulin, its teratogenicity, carcinogenicity and mutagenicity is known and is of concern.

The Codex Alimentarius Commission as part of the United Nations joint FAO/WHO Food Standards Programme in their 28th Session (June 1997) in respect of patulin indicates a PMTDI (Provisional Maximum Tolerable Intake) of 0.4 micrograms per kilogram body weight per day (i.e. 0.4 micrograms/kg.bw/day). It was reported that apple juice can occasionally be heavily contaminated notwithstanding that apple juice generally (particularly single strength apple juice eg; 11.5.degree. Brix) has patulin levels of below 50 micrograms per liter. The lower recommendations (eg; to below 25 micrograms of patulin per liter or even lower) are now being considered and recommended. It is known that in some apple juice samples (where there is a significant use of windfall and/or rotting fruit) to be as high as 1500 microgram/l. However apple juice more commonly contains patulin up to 200 microgram/l.

U.S. Pat. No. 6,248,382 Miller et al. describes process for reducing the patulin concentration in fruit juices which includes presenting the juice to a resin material having in abundance micropores of less than 20.ANG. minimum pore width and at least a pore surface capable of retaining patulin by the forces of chemisorption. Preferably the resin has weak base functionality and is substantially devoid of mesopores and macropores. The resin preferably has a surface area of greater than 900 $m^2/g$ (BET) and the resin has been hypercross-linked whilst in the swollen state. Regeneration involves the conversion of the resin held patulin to a more easily flushed out derivative using ammonia or a volatile base, preferably generated in situ from a high pH solution.

S. Drusch et al. investigated the stability of patulin in an aqueous juice-like model system. At acidic pH, the presence of ascorbic acid reduced the stability of patulin. After 34 days, patulin was reduced to 30% of its initial concentration in the presence of ascorbic acid compared to 68-71% in samples without ascorbic acid. Conditions during storage (presence of light, oxygen and/or metal ions) influenced the stability of patulin. Furthermore, it was possible to induce degradation of patulin by either generating hydroxyl radicals or by adding the rather stable radical diphenyl-1-picrylhydrazyl (DPPH). Data this study indicate that patulin is decomposed by free radicals generated by oxidation of ascorbic acid to dehydroascorbic acid. Rapid oxidation of ascorbic acid in the presence of oxygen, catalysed by free metal ions, resulted in a decrease of patulin. After complete oxidation of ascorbic acid, no further patulin degradation was observed. In contrast, slow oxidation of ascorbic acid in the presence of metal-chelators induced a continuous, slow oxidation of patulin. Due to low oxygen content in the headspace of a food package, addition of ascorbic acid to products such as apple juice, prior to filling, cannot be considered as an effective decontamination strategy [Stability of patulin in a juice-like aqueous model system in the presence of ascorbic acid S. Drusch, S. Kopkaa and J. Kaedinga Food Chemistry Volume 100, Issue 1, 2007, Pages 192-197].

Proteins, including those in fruit juices, can cause protein contact dermatitis in sensitive individuals. Shortly after contact with the causative proteinacous material, such individuals can experience symptoms such as acute urticarial or vesicular eruption on the skin, often accompanied by pruritus, burning, and/or stinging [V. Janssens, et al., "Protein contact dermatitis: myth or reality?", British Journal of Dermatology 1995; 132: 1-6].

Thus, it is highly desirable to obtain and use apple juice that contains as little patulin and as little protein as possible: and a significant task exists in simultaneous removing or substantially reducing the concentrations of patulin and protein in apple juice.

SUMMARY OF THE INVENTION

The present invention also relates to a method for isolating bioactive fractions that are derived from fruit juices and are free or substantially free of protein and patulin. The present invention also relates to a method for preparing a bioactive fractions derived from fruit juices that are stabilized and are either free of or substantially free of patulin and protein.

DETAILED DESCRIPTION OF THE INVENTION

The present invention provides a commercially viable process for removing or substantially reducing the patulin and protein content in fruit juices. The primary objective of this invention is patulin and protein removal or substantiate reduction of their content in bioactive ingredients (fractions) obtained from various apple cultivars (Granny Smith, Golden Delicious, Gala, Cameo, McIntosh, Braeburn, etc.); however, there is no reason to expect that patulin and protein content will not be reduced in bioactive fractions (ingredients) obtained from other fruit juices (e.g. peaches, pears, bananas, plums, apples, pineapples, apricots, cherries, grapes, blueberries, raspberries, blackberries, cranberries, tangerines, prickly pears, nectarines, pomegranates, oranges, grapefruit, tomatoes, and combinations or mixtures thereof) with the use of described process.

As used herein, "substantially free of patulin" means less than 25 microgram/kg content that is determined by the official method of analysis of the association of Official Analytical Chemists (AOAC) 995.10, Patulin in Apple Juice.

As used herein, "substantially free of proteins" means less than 0.1% total protein content determined by hydrolyzed and un-hydrolyzed amino acid analysis conducted on Hitachi L-8900 amino acid analyzer.

The formulations containing the bioactive fractions (ingredients) of the present invention may be prepared using methodologies that is well known by an artisan of ordinary skill.

As used herein, "topical application" generally refers to techniques relating to directly laying on or spreading the bioactive ingredients of the present invention or formulations containing these bioactive ingredients onto the outer skin using, e.g., by use of the hands or an applicator such as a wipe. The bioactive ingredients of the present invention are "cosmetically acceptable."

As used herein, the term "cosmetically acceptable" refers to bioactive ingredients, formulations, cosmetically active agents, or inert ingredients that are suitable for use in contact with mammalian tissues (e.g., the skin of humans) without undue toxicity, incompatibility, instability, irritation, allergic response, and the like, commensurate with a reasonable benefit/risk ratio.

It should be noted that, depending on conditions of fruit (e.g. apple) cultivation, year of growth, and particular harvest, the dry matter content in fruit can vary and it may impact the consistency of fruit juice properties and thus reproducibility of fruit juice derived bioactive fractions (ingredients).

The present invention allows for the standardization of initial fruit juice properties to improve reproducibility of bioactive (fractions) ingredients. The standardization of initial fruit juice properties can be improved by exploring uniform conditions for apple cultivation and harvesting.

The isolated bioactive fractions (ingredients) are combined with a stabilizing agent. Particularly suitable stabilizing agents can include, without limitation, a preservative, a stabilizer and/or mixtures thereof. The isolated bioactive ingredients can be further concentrated and then stabilized for further utilization in skin care for topical, oral and functional drink applications. The bioactive ingredients of the present invention can further be included in delivery systems that are commonly used in the art.

An exemplary method of preparing the isolated bioactive fractions derived from fruit juices that are either free of or substantially free of patulin and protein involves harvesting, collecting, and washing of the fresh fruit. Suitable steps to follow for preparing the fresh fruit biomass include, for example, the following: (1) preservation of the inherent moisture content of the fruit; (2) preservation of fruit integrity during harvesting; (3) minimization of environmental impact and time factors of biological degradation of the fruit biomass; and (5) cleaning of the fruit biomass prior to processing (e.g., prior to grinding and maceration). Each of these steps is discussed below.

Preservation of Inherent Moisture Content:

The harvest should be done to avoid wilting due to moisture loss. Optimal conditions are those where natural moisture content is maintained and preserved.

Preservation of Fruit Integrity During Harvesting:

Harvesting of the fruit biomass is conducted in a manner that avoids or minimizes the chopping, mashing, crushing, or other type of injury of the fruit. For large-scale industrial harvesting, where it may not be possible to avoid chopping due to the type of equipment required, care is taken to minimize injury that could lead to microbial growth, moisture loss, intensification of oxidation, polymerization, isomerization, and hydrolysis processes (i.e., unwanted catabolic processes) in collected fruit. Further, particular attention is made to minimize injury during and after harvest.

Minimization of Environmental Impact and Time Factors of Degradation:

Delivery time of the fruit material to the processing facility and exposure of biomass to sun, high temperature, and other negative environmental factors, should be minimized to prevent the impact of unwanted degradation processes as described above. For example, in one embodiment of the present invention, the delivery time for the fruit for further processing does not exceed 30 minutes from the time of harvest. In another embodiment, fruits that undergo long distance transport are treated to a post-harvest procedure involving immediately placing the fruit biomass into Styrofoam coolers containing bags of frozen gel packs to help maintain freshness and natural moisture content during overnight delivery to the processing facility. As a nonlimiting example, for many fruit species it is beneficial to not only minimize delivery time for processing, but to also keep the fruit material cool, by refrigeration if necessary, to prevent and/or minimize unwanted degradation prior to and/or during processing.

Cleaning Step Prior to Grinding and Maceration:

A washing step to remove debris from the fruit prior to further processing is performed once the fruit is harvested. The washing is achieved using a low-pressure rinse for a short duration under conditions to prevent the initiation of the release of the juice from the fruit, to cause injury, or to remove valuable components. For example, in one embodiment of the present invention, the washing of the fruit biomass was accomplished in less than or equal to 5 minutes with a water pressure of less than or equal to 1 $kg/cm^2$. Residual water wash did not contain any green or yellow pigments, which indicates the absence of subsequent injury. The excess water is removed from washed fruit biomass in order to keep the dry matter content close to natural level.

After the fruit is harvested, as described above, further processing of the fruit is performed to yield fruit juice. In one embodiment, the fruit biomass is subjected to grinding, maceration, and pressing to separate the intracellular content, i.e., the fruit juice, and to separate it from the fiber-enriched press-cake containing predominantly cell walls.

An example of a suitable processing protocol involves the steps described below. A hammer mill may be used to grind the fruit to yield fruit tissue particles of a small size in a short time and without significant increase of biomass temperature. In one embodiment, a modified hammer mill is used to produce the maximum size of macerated fruit particles less than or equal to 0.5 centimeters during less than or equal to 10 seconds of treatment, where the increase of biomass temperature is less than or equal to 5° C.

Exposure of ground and macerated fruit biomass is minimized to prevent the impact of unwanted catabolic processes, as described above. The separation of fruit juice from fiber-enriched material (or press-cake) is commenced as soon as possible after grinding and maceration of the fruit biomass. The fruit biomass is processed in a short time and without significant increase in temperature. In one embodiment, immediately after grinding and maceration, the fruit biomass is pressed using a horizontal, continuous screw press (Compact Press "CP-6", Vincent Corporation, FL). The pressure on the cone is maintained at level 24 $kg/cm^2$, screw speed is at 12 rpm, and biomass temperature increase is less than or equal to 5° C.

The initial fruit juice usually contains small fiber particles, starch, pectic substances, hemicellulose and cellulose particles which can absorb valuable fruit juice components and also block the hoses and pumps. The above particles should be removed by filtration or low-speed centrifugation. For example, the initial fruit juices produced after the pressing step are filtered through four layers of nylon fabric prior to using the fruit cell juice in the methods of the present invention.

Once fruit juice is separated, the fruit cell juice is relatively stable colloidal dispersion in which organelles represent the dispersed phase and cytoplasm represents the continuous phase. Fruit juice is then treated to a processes involving (1) triggering destabilization of above colloidal dispersion performing a "initiation of membrane fraction aggregation step" to yield a destabilized fruit juice and (2)

performing a "membrane fraction separation step" on destabilized cell juice mixture to yield a membrane fraction (containing nucleous, mitochondria, or combination of thereof) and a fruit juice supernatant. In one embodiment, initiation of membrane fraction destabilization is accomplished by subjecting said cell juice to electromagnetic waves at a frequency of 2.45 GHz. In another embodiment the frequency employed is greater than 2.45 GHz up to 7.0 GHz. In another embodiment, the frequency employed is any frequency between 2.45 and 7.0 GHz effective to achieve destabilization of the membrane fraction. After destabilization is achieved, a membrane fraction separation step is performed. This step includes, for example, separating of destabilized fruit juice into the membrane fraction and the fruit juice supernatant using separating techniques including filtration, or centrifugation, or combination of thereof.

A variety of instruments can be employed in the process of the invention in order to generate the electromagnetic waves necessary to destabilize the fruit juice including, but not limited to magnetrons, power grid tubes, klystrons, klystrodes, crossed-field amplifier, travelling wave tubes, and gyrotrons. One such instrument includes, but is not limited to high power magnetron. Conventional and industrial magnetrons operate at a frequency of 915 MHz and 2.45 GHz and can be employed. However at those frequencies undesirable heat is can be generated that can denature the cell juice composition. It is therefore advantageous to use electromagnetic waves operating at frequencies that are substantial higher than the frequencies of conventional or industrial magnetrons, which allows for destabilization of the fruit juice without undesirable denaturing due to heat generation. This frequency is typically above the frequency of conventional microwave magnetrons, i.e., above 2.45 GHz, in another embodiment greater than 2.45 GHz and less than about 7 GHz; in another embodiment from about 3 to about 6 GHz, and in yet another embodiment, any frequency between 2.45 and 7.0 GHz effective to achieve destabilization of the fruit juice. During the destabilizing step of the invention the temperature of the fruit juice is beneficially maintained below 40° C., in another embodiment below about 35° C., in another embodiment below about 30° C., in another embodiment below about 25° C., in another embodiment below about 20° C.

The freshly obtained membrane fraction is a paste having color and specific odor that is raw material source specific. The membrane fraction is represented predominantly by hydrophobic compounds present in the fruit. The composition of the membrane fraction includes predominantly phospholipids, membrane proteins, chromoplasts, traces of chloroplasts, traces of chlorophyll, nucleus, mitochondria and carotenoids.

After the bioactive fractions derived from fruit juices that are either free of or substantially free of patulin and protein is produced, it is then subjected to the stabilizing step to yield stabilized fruit juice. In one embodiment, the stabilizing step involves incubating the bioactive fraction in a mixture of at least one preservative, at least one antioxidant and at least one stabilizer to yield a stabilized bioactive serum fraction. Suitable preservatives, antioxidant and stabilizers for use in the present invention include, for example, potassium sorbate, sodium benzoate, sodium metabisulfite and pentylene glycol.

The present invention also relates to a bioactive topical formulation suitable for topical application to mammalian skin and/or hair. The composition can be a leave-on product such as, for example, a cream, dressing, gel, lotion, ointment, liquid, a spray applicator, and combinations thereof or a wash-off product such as for example a hand dishwashing detergent, liquid hand soap, bar soap, body wash, shampoo, general purpose cleanser, and combinations thereof.

In one embodiment, the bioactive topical formulation includes a topically effective amount of the bioactive composition of the present invention. The bioactive topical formulation can further include a topically acceptable carrier. Suitable topically acceptable carriers can include, without limitation, a hydrophilic cream base, a hydrophilic lotion base, a hydrophilic surfactant base, a hydrophilic gel base, a hydrophilic solution base, a hydrophobic cream base, a hydrophobic lotion base, a hydrophobic surfactant base, a hydrophobic gel base, and/or a hydrophobic solution base. In one embodiment, the bioactive composition can be present in an amount ranging from between about 0.001 percent and about 90 percent of the total weight of the bioactive topical formulation.

The following examples are intended to illustrate particular embodiments of the present invention, but are by no means intended to limit the scope of the present invention.

Example 1—Preparation of Bioactive Fractions (Ingredients) from Apple Fruit (Granny Smith Cultivar)

Below is a description of relevant aspects of one embodiment of the method of the present invention.

The apple whole fruits are collected directly from the trees at the apple farm. Inspection and removal of unsound fruits is conducted. After that the apples are thoroughly washed in filtered city water before processing. The whole fruits are then grinded (macerated), pressed and filtered to produce initial fruit juice, the initial source of cosmetic ingredient Recentia® PM [INCI: *Pyrus malus* (Apple) Juice], CAS RN 1310712-55-0 or functional drink ingredient Purecentia™ PM.

The yield of initial apple fruit juice from apple fruits after grinding, pressing and filtration is about 63 to 69% weight/weight.

The initial fruit juice is then subjected to various treatments including pH adjustments, focused microwave irradiations and separations by centrifugations and filtrations. The pH of initial juice and interim supernatants are adjusted with dilute hydrochloric acid (HCl) solution (5N) or sodium hydroxide (NaOH) 25% solution prior to focused microwave processing steps. The pH of initial apple juice that is about 3.2 to 3.6 is adjusted using a titration method utilizing 5 N Hydrochloric Acid (HCl) to decrease the pH of the cell juice to about 3.0. Then the pH adjusted fruit juice is immediately exposed to microwave irradiation using specially designed continuous flow system having 2.45 GHz frequency and 3,200 Watt output power (Microwave Research & Applications, Inc., Laurel, Md.). This system is equipped with constant speed stirrer BDC 1850 (Caframo Ltd., Wiarton, Ontario, Canada) and a temperature control probe. This treatment continued until the temperature of the fruit juice in microwave chamber reached about 92 to 96° C. and then the treated fruit juice is immediately pumped through a continuous flow centrifuge device which is connected with a 1 HP recirculating chiller (Model 6106 P, Polyscience Corporation, Niles, Ill.) to yield a supernatant 1 and precipitate 1. The pH of supernatant 1 is then adjusted using a titration method utilizing 25% solution of Sodium Hydroxide (NaOH) to increase the pH of the supernatant 1 from about 3.0 to about 8.0. Then the pH adjusted supernatant 1 is immediately exposed to microwave irradiation using specially designed continuous flow system having 2.45 GHz frequency and 3,200 Watt output power (Microwave Research & Applications, Inc., Laurel, Md.). This system is equipped with constant speed stirrer BDC 1850 (Caframo Ltd., Wiarton, Ontario, Canada) and a temperature control probe. This treatment continued until the temperature of the supernatant 1 in microwave chamber reached about 92 to 96° C. and then the treated supernatant 1 is immediately pumped through a continuous flow device which was connected with a 1 HP recirculating chiller (Model 6106 P, Polyscience Corporation, Niles, Ill.) to produce the supernatant 2 and precipitate 2.

The pH of supernatant 2 is then adjusted using a titration method utilizing 5 N Hydrochloric Acid (HCl) to decrease the pH of the supernatant 2 to from pH about 8.0 to pH about 3.0 and centrifuged again to yield the supernatant 3 and precipitate 3. Appropriate preservatives and stabilizers are then added to supernatant 3 to yield Recentia® PM or Purecentia™ PM.

Dose rate of microwave treatments were about 1380 joules/sec. During focused microwave irradiation steps there is no concentration of juice supernatants due to the evaporation. The system that is used is completely sealed and prevents any loses of intracellular water due to the evaporation.

The temperatures during the process are regulated, monitored and controlled throughout the process and are kept below 30° C. with the exception of the microwave treatments where temperature is increased to about 92 to 96° C. at which point it is immediately and rapidly cooled back to below 30° C. It was unexpectedly found that the biological constituents remaining in cosmetic ingredient Recentia® PM or functional drink ingredient Purecentia™ PM are water soluble components of the initial apple juice that are free or substantially free from patulin and protein.

Example 2—Characteristics and Properties of Bioactive Ingredient Recentia® PM [INCI: *Pyrus malus* (Apple) Juice]

Bioactive Ingredient Recentia® PM [INCI: *Pyrus malus* (Apple) Juice] was prepared according to the process described in Example 1.

Analyses of Bioactive Ingredient Recentia® PM were conducted to determine its various physico-chemical and microbial characteristics.

The selected physico-chemical characteristics of Recentia® PM [INCI: *Pyrus malus* (Apple) Juice] and test methods are presented below in Table 1.

TABLE 1

The selected physico-chemical characteristics of Recentia ® PM [INCI: *Pyrus Malus* (Apple) Juice] and test methods.

| Property | Minimum | Maximum | Test Method | Units |
|---|---|---|---|---|
| Appearance | Clear to Yellow Liquid | Clear to Yellow Liquid | Determined organoleptically. | N/A |
| Odor | Characteristic | Characteristic | Determined organoleptically. | N/A |
| Color | 0.5 | 7.0 | Determined on Lovibond Comparator 3000 Gardner Scale, Turn on comparator lamp. Measure 8 mL of sample into sample tube. Insert tube into comparator. Rotate the knobs until two color standards nearest in color to the sample have been located. Record the value of the sample color accordingly. If the color of the sample is substantially similar to both, rather than a single standard, then record it as a value between the values of the two standards. | Gardner scale |
| Dry Matter | 9.0 | 14.7 | Dry matter is determined by comparing the weights of liquid sample with residual dry matter after water has been evaporated. Procedure is based on standard laboratory practices commensurate with available equipment. Take three disposable aluminum weighing dishes (VWR 25433-016) and distinctly number them with a permanent marker on the outside. Allow marker ink to dry. Turn on the Ohaus Explorer E00640 balance (Ohaus Corporation) and allow it to start up. Zero the weight. Place a dish on the balance and record the weight for that dish as 'tare'. Without removing the dish from the balance, add approximately 4 mL of liquid sample and record the weight for that dish as 'tare + wet'. Set the dish with sample aside. Repeat the above with two remaining dishes. Leave the dishes for 24 hours in the ThermoScientific "Lindberg Blue M" Gravity oven at 105 degrees Celsius. Remove the dishes and allow them to cool for approximately 5 minutes at room temperature. Weigh each dish with dried residue individually and record the weight as 'tare + dry'. Dry matter percentage is calculated as ('tare + dry' − 'tare')/('tare + wet' − 'tare') * 100. Record dry matter percentage for the sample as mean of dry matter percentage for the three dishes. | % |
| Refractive index | 1.350 | 1.360 | Determined by measuring on Reichert Arias 500 refractometer with temperature regulation provided by Cole-Parmer Polystat temperature controller, model number 12108-10. Procedure is based on the instruction manual for Arias 500 refractometer, sections 6.0, 4.1 and 4.4-4.5. Turn on the temperature controller, set temperature to 20 degrees Celsius. Turn on refractometer. Ensure that Automatic Reading Method is enabled. Deposit approximately 0.5 mL of deionized water on the surface of the lower measuring | nD |

TABLE 1-continued

The selected physico-chemical characteristics of Recentia ® PM
[INCI: *Pyrus Malus* (Apple) Juice] and test methods.

| Property | Minimum | Maximum | Test Method | Units |
|---|---|---|---|---|
| | | | prism. Close the cell, taking care to avoid bubble formation. Turn shadowline adjustment knob to bring the shadow line within the crosshairs. Wait for temperature at refractometer measuring cell to completely stabilize, then push Read button. Retry above steps until refractive index of deionized water is determined as 1.333 at least three times in a row. Rinse the lower and upper surfaces of the measuring cell with deionized water and blot dry with lint-free wipe. Deposit approximately 0.5 mL of sample on the surface of the lower measuring prism. Close the cell and turn the shadowline adjustment knob to bring the shadowline within the crosshairs. Wait for temperature at refractometer measuring cell to completely stabilize, then push Read button and note the reading. Rinse the lower and upper surfaces of the measuring cell with deionized water and blot dry with lint-free wipe. Repeat above steps until stable readings have been obtained for sample material at least three times in a row. Record the value of these stable readings as refractive index of the sample material. | |
| Density | 1.03 | 1.08 | Determined with Densito 30PX densitometer from Mettler Toledo. Procedure is based on Operating instructions for Densito 30PX, sections 4 and 6. Push and hold the power button on the densitometer for a second to turn it on. Once the instrument starts up, ensure that the display is set to g/cm3 units. Depress the plunger button fully, submerge the sampling tube in deionized water and slowly push the fill trigger to fill the sample loops with 4 cm3 of deionized water. Avoid bubble intake or formation. Note the reading. If it deviates by more than 0.05% from expected density of water at the ambient temperature, recalibrate the densitometer as per Operating Instructions. After ensuring that the unit display and calibration for densitometer are proper, eject the water into a waste receptacle by depressing the plunger button fully. Submerge the sampling tube in liquid sample and push the fill trigger to fill the sample loops with 4 cm3 of sample. Avoid bubble intake or formation. Note the reading once it stabilizes. Eject the sample from densitometer into a waste receptacle and repeat steps above for additional readings, until receiving three matching readings in a row. Record that as the value of density (specific gravity) for the sample. | $g/cm^3$ |
| pH | 3.0 | 5.0 | Determined by measuring on a pH meter such as Denver Instrument Model 250 pH/ISE/conductivity meter with pH/ATC electrode number 300729.1. Procedure is based on Denver Instrument Company 301127.1 Rev. D manual, pages ii and 9 through 12. Turn on the meter and wait for the software to start up. Push Cal Data button, select pH channel and press Enter. Check that the calibration is current and slope within acceptable parameters - manual recommends between 90% and 105%. For product specification determination, used values between 95% and 100%. If calibration is out of date or slope outside acceptable boundaries, open the window on the pH electrode and rinse the electrode head in deionized water. Then push the Standardize button, select pH channel and press Enter. Select Manual Buffer Entry and press Enter. Type in the pH value of a standardization buffer and press Enter. Submerge the head of the pH electrode into a small beaker of the buffer, stirred on a magnetic stirrer and press Enter. Wait for the reading to stabilize. Repeat the above steps with two additional buffers to complete three-point calibration. If calibration slope is outside acceptable parameters, repeat. The pH buffers used to calibrate the pH meter during the product specification determination were acquired from Thermo Electron Company. In particular, Orion Application Solution number 910107 was used as pH 7.00 standard, Orion Application Solution number 910104 was used as pH 4.01 standard, and Orion Application Solution number 910110 was used as pH 10.01 standard. After ensuring that pH meter calibration is current and within acceptable bounds, rinse the pH electrode head with deionized water and blot it lightly with a lint-free wipe. Pour approximately 20 mL of a sample to be tested into a small beaker. Add a magnetic stir bar and set it to be stirred at a low speed on a magnetic stirrer. Ensure that the window | N/A |

TABLE 1-continued

The selected physico-chemical characteristics of Recentia ® PM
[INCI: *Pyrus Malus* (Apple) Juice] and test methods.

| Property | Minimum | Maximum | Test Method | Units |
|---|---|---|---|---|
| UV max | 260 | 265 | at the base of pH electrode is open, submerge the electrode head in liquid sample and wait for pH reading to stabilize. Record the stable reading as the pH value for the sample. Determined on Ultrospec 9000 UV/Visible dual-beam spectrophotometer (GE Healthcare Life Sciences) with 5-position thermostatted cell changer. The procedure is based on chapter 10 section 3 of GE Healthcare Ultrospec 7000/8000/9000 UV/Visible Spectrophotometers User Manual and chapter 4 section 3 of GE Healthcare Life Sciences Datrys Life Science Manual version 2.2.0.0. Instrument control is provided by Datrys Life Science software version 2.2.0.0 (GE Healthcare) on the attached computer and/or built-in application suite of the device. Temperature regulation is provided by CB20 Mini Circulator (Torrey Pines Scientific). Turn on the circulator and set the temperature to 20 degrees Celsius and pump speed to 50%. Turn on the spectrophotometer and/or the attached control computer and wait for the startup procedures to finish. Take two quartz spectrophotometer cuvettes with 1 cm path length and volume of at least 3 ml. Dispense 3 mL deionized water into the cuvette which will be used as the blank, and 2.998 mL deionized water into the cuvette which will hold the sample. Add 2 microliters of liquid sample to the sample cuvette with micropipettor, for effective 1 in 1500 v/v dilution. For materials that absorb UV light especially strongly or especially weakly, a different dilution may be required. Close the two cuvettes with cuvette caps and mix by repeated inversion while avoiding bubble formation. Open spectrophotometer sample compartment cover. Place the blank cuvette into the reference cell holder and the sample cuvette into the position number 1 in the cell changer. Make sure that clear sides of the cuvettes are the ones which will be facing the beam. Close the cover and wait to allow the cuvette temperature to equilibrate at 20 degrees Celsius. Perform a scan and analysis using the following parameters: start wavelength 200.0 nm, end wavelength 400.0 nm, step 0.5 nm, bandwidth 1 nm, fast scan speed, lamp mode set as pulse, reading mode set as absorbance, feature type set as "Peaks", detection set as "Sensitive". Report the wavelength of characteristic peak as λ max. In case of extremely broad and shallow peaks, detection may be set as "Custom" with appropriate minimum peak height. In case of no identifiable peaks being present in the plot, λ max is the wavelength of maximum absorbance. These tasks may be accomplished in the "Wavescan" application in built-in instrument control software, or "Wavelength Scan" application in Datrys Life Science version 2.2.0.0 software running on attached control computer. | nm |
| Total Plate Count | <10 | <10 | Determined as per US Pharmacopoeia XXX, NF25, <61>, Microbiological Limit Tests | CFU/gm |
| Mold/Yeast | <10 | <10 | Determined as per US Pharmacopoeia XXX, NF25, <61>, Microbiological Limit Tests | CFU/gm |
| *E. coli* | Negative/10 gm | Negative/10 gm | Determined as per US Pharmacopoeia XXX, NF25, <61>, Microbiological Limit Tests | CFU/gm |
| *Salmonella* sp. | Negative/10 gm | Negative/10 gm | Determined as per US Pharmacopoeia XXX, NF25, <61>, Microbiological Limit Tests | CFU/gm |
| *Slaphylococcus aureus* | Negative/10 gm | Negative/10 gm | Determined as per US Pharmacopoeia XXX, NF25, <61>, Microbiological Limit Tests | CFU/gm |
| *Pseudomonas* sp. | Negative/10 gm | Negative/10 gm | Determined as per US Pharmacopoeia XXX, NF25, <61>, Microbiological Limit Tests | CFU/gm |
| Patulin | Not detected (Below the method detection limit of 1 microgram/kg (or 0.001 ppm) | <25 | By the official method of analysis of the association of Official Analytical Chemists (AOAC), Patulin in Apple Juice. | Microgram/kg |
| Protein | <0.03 | <0.1 | Amino acid analysis conducted on Hitachi L-8900 amino acid analyzer. | % |

Recentia® PM and Purecentia™ PM are readily soluble in water in any proportion and are biodegradable ingredients. Recentia® PM satisfies skin care industry requirements regarding total plate count, mold and yeast count, and absence of pathogens.

Recentia® PM and Purecentia™ PM have an effective system of preservatives.

Recentia® PM and Purecentia™ PM were determined to be stable (i.e., maintaining physical and chemical integrity) for at least 12-18 months while stored at a temperature of between 4 and 25 degree. C. in a closed container protected from light.

Table 2 includes the data related to free radical scavenging activity of Recentia® PM.

TABLE 2

DPPH (2,2-Diphenyl-1-Picrylhydrazyl) free radical scavenging activity of Recentia ® PM

| Material | CAS RN# | DM % w/w | mg DPPH/g sample (as supplied) |
|---|---|---|---|
| Recentia ® PM Lot A30510MSS-0551 | 1310712-55-0 | 13.33 | 6.02 |

Method

DPPH (2, 2-Diphenyl-1-Picrylhydrazyl) free radical scavenging activity was determined by a kinetic colorimetric assay adapted for use with glass-coated polypropylene 96-well microtiter plates (catalog number 400 062) from SUN-SRi (Rockwood, Tenn.) and Synergy 2 microplate reader from BioTek Instruments Inc (Winooski, Vt.). Absorbance was measured at 515 nm wavelength. Reaction volume in each microplate well was 200 µl, with initial concentration of DPPH equal to 114 µM. L-ascorbic acid was used as positive control. DPPH (Sigma D9132) and USP L-ascorbic acid (Sigma A-2218) were obtained from Sigma-Aldrich (St. Louis, Mo.). Stoichiometry of the reaction was calculated and expressed as units weight test article necessary to quench 1 unit weight DPPH. This can easily be recalculated as DPPH equivalent per sample weight. This method was adapted from procedure described in "Use of a free radical method to evaluate antioxidant activity" by W. Brand-Williams et al, published in LWT—Food Science and Technology, Volume 28, Issue 1, 1995, pp 25-30.

What is claimed is:

1. A composition comprising a bioactive fraction derived from fruit juice of an Apple (*Pyrus malus*) produced by processing the fresh fruit of Apple under conditions effective to yield a fruit juice substantially free of protein and patulin, said processing the fresh fruit comprising:
   (i) separating the fresh fruit into an initial fruit juice and a fiber enriched precipitate;
   (ii) subjecting the initial fruit juice to electromagnetic waves at a frequency from 2.45 GHz up to 7.0 GHz, while maintaining the temperature below 40° C., to yield a first fruit juice supernatant and a first precipitate;
   (iii) subjecting said first juice supernatant to electromagnetic waves at a frequency from 2.45 GHz up to 7.0 GHz, while maintaining the temperature below 40° C. to yield a second fruit juice supernatant and a second precipitate;
   (iv) subjecting said second fruit juice supernatant to centrifugation and filtration steps to yield a third fruit juice supernatant and a third precipitate;
   wherein the said third fruit juice supernatant is the bioactive fraction and comprises less than 25 microgram/kg patulin and less than 0.1% total protein content,
   wherein the composition is used as an antioxidant and a free radical scavenging composition.

2. The composition according to claim 1, wherein in step (ii) the temperature is maintained below about 35° C.

3. The composition according to claim 1, wherein in step (ii) the temperature is maintained below about 30° C.

4. The composition according to claim 1, wherein in step (ii) the temperature is maintained below about 20° C.

5. The composition according to claim 1, wherein the electromagnetic waves are generated by a magnetron, power grid tube, klystron, klystrode, crossed-field amplifier, travelling wave tube, and/or a gyrotron.

6. The composition according to claim 1, wherein the said bioactive fraction is further incubated in a mixture of at least one preservative, at least one antioxidant, at least one stabilizer or mixtures or combinations thereof to yield a stabilized bioactive fraction.

7. The composition according to claim 6, wherein said preservatives, antioxidant and/or stabilizers are selected from potassium sorbate, sodium benzoate, sodium metabisulfite, pentylene glycol or mixtures or combinations thereof.

8. The composition according to claim 6 for use in oral and functional drink applications.

9. The composition according to claim 1, wherein the composition is a leave-on product selected from the group consisting of cream, dressing, gel, lotion, ointment, liquid, a sprayable composition, and combinations thereof, or a wash-off product selected from the group consisting of hand dishwashing detergent, liquid hand soap, bar soap, body wash, shampoo, general purpose cleanser, and combinations thereof.

10. The composition according to claim 1 further comprising a topically acceptable carrier.

* * * * *